(12) United States Patent
Shinno et al.

(10) Patent No.: US 9,668,943 B2
(45) Date of Patent: Jun. 6, 2017

(54) DENTAL CONDITIONING COMPOSITION

(71) Applicant: KABUSHIKI KAISHA SHOFU, Kyoto (JP)

(72) Inventors: Kazuya Shinno, Kyoto (JP); Akihiro Nagafuji, Kyoto (JP); Shingo Tateishi, Kyoto (JP); Daisuke Hara, Kyoto (JP); Yoshiyuki Jogetsu, Kyoto (JP)

(73) Assignee: KABUSHIKI KAISHA SHOFU, Kyoto (JP)

( * ) Notice: Subject to any disclaimer, the term of this patent is extended or adjusted under 35 U.S.C. 154(b) by 0 days.

(21) Appl. No.: 14/809,759

(22) Filed: Jul. 27, 2015

(65) Prior Publication Data
US 2016/0030294 A1 Feb. 4, 2016

(30) Foreign Application Priority Data

Aug. 1, 2014 (JP) .................................. 2014-158169

(51) Int. Cl.
*A61K 6/00* (2006.01)
*C08L 33/02* (2006.01)

(52) U.S. Cl.
CPC .......... *A61K 6/0023* (2013.01); *A61K 6/0017* (2013.01); *A61K 6/0029* (2013.01)

(58) Field of Classification Search
CPC ............................ A61K 6/0023; A61K 6/0029
USPC ........................................................ 523/118
See application file for complete search history.

(56) References Cited

U.S. PATENT DOCUMENTS

| | | | |
|---|---|---|---|
| 5,258,067 A | 11/1993 | Podszun et al. | |
| 5,707,611 A | 1/1998 | Ikemura et al. | |
| 2002/0018755 A1* | 2/2002 | Jia et al. | A61K 8/24 424/49 |
| 2007/0009449 A1 | 1/2007 | Kanca, III | |

FOREIGN PATENT DOCUMENTS

| | | |
|---|---|---|
| AU | 2010201886 | 12/2011 |
| DE | 38 21 578 | 12/1989 |
| JP | 5-163111 | 6/1993 |
| JP | 5-246817 | 9/1993 |
| JP | 10-81611 | 3/1998 |
| JP | 3505182 | 12/2003 |

OTHER PUBLICATIONS

Extended European Search Report issued Dec. 21, 2015 in corresponding European Application No. 15178092.1.

* cited by examiner

*Primary Examiner* — Tae H Yoon
(74) *Attorney, Agent, or Firm* — Wenderoth, Lind & Ponack, L.L.P.

(57) ABSTRACT

A dental conditioning composition that enhances the adhesiveness of any dental material for a tooth surface by suppressing any excessive demineralization for the tooth surface and improving the polymerization activity of a dental adhesive composition by causing a polymerization catalyst included in the dental conditioning composition of the present invention to remain on the tooth surface. A dental conditioning composition having a gel character, that includes a polymerization catalyst, an acidic compound, water, and a thickening agent, and whose pH (the hydrogen ion exponent) is in a range from 0.1 to 0.9.

4 Claims, 2 Drawing Sheets

DENTAL CONDITIONING COMPOSITION

TECHNICAL FIELD

The present invention relates to a dental conditioning composition used in a tooth surface treatment executed before application of a dental adhesive composition when such a dental material is caused to adhere to the tooth surface using the dental adhesive composition, as an orthotic material, a pit and fissure plugging material, a restoration material, a dental crown material, a prosthetic material, a dental abutment construction material, or a root canal material. More particularly, the present invention relates to a dental conditioning composition usable for both of unground enamel to be bonded when the orthotic material, the pit and fissure plugging material, etc., is bonded thereto, and the enamel and the dentine after a cavity is formed to be bonded when the restoration material, the dental crown material, the prosthetic material, the dental abutment construction material, the root canal material, etc., is bonded. Furthermore, the present invention relates to a dental conditioning composition characterized in that the tooth surface treated using the dental conditioning composition of the present invention (the unground enamel, or the enamel and the dentine after formation of a cavity) is little damaged by demineralization and is provided with higher functionality to improve its adhesion performance.

BACKGROUND ART

In the related art, when a dental material such as an orthotic material, a pit and fissure plugging material, etc., is adhered to unground enamel, an operative procedure for the adhesion has been employed according to which the dental material is brought into pressurized contact with or packed on the enamel surface to which acid treatment is applied by applying an acid etching material to the unground enamel, washing the enamel with water, and drying the enamel. With this operative procedure for the adhesion using the acid etching material, a roughly surface is formed by the demineralization of the enamel due to the acid etching material and adhesive performance is developed by micro mechanical fitting based on permeation and hardening of the dental material. The acid etching material is generally a liquid, therefore, it has excellent workability at the application step. However, the acid etching material has high fluidity and has a disadvantage that the acid etching material flows to and permeates into the outside of the target portion. Problems are therefore also pointed out such as induction of secondary dental caries due to exposure of the demineralized portion when the acid etching material flows to the outside of the target portion.

It is also pointed out that the organic component (collagen) in the dentine is denatured, the collagen shrinks during air-drying and the shrinked-collagen raises a degradation of the adhesive strength when the acid etching material is applied to the dentine after a cavity is formed.

In addition to the traditional method of causing a dental material to adhere to the tooth surface by applying a dental adhesive composition after executing the acid treatment using the acid etching material, an adhesion method has recently been proposed according to which the tooth surface and the dental material are adhered to each other by applying a dental adhesive composition without executing any acid treatment using the acid etching material. The dental adhesive composition used in this case has an adhesive monomer having an acidic group in its molecule (hereinafter, referred to as "acidic monomer") blended therein and can thereby concurrently execute the acid treatment to demineralize the tooth surface and primer treatment to cause the monomer to permeate. As above, the dental adhesive composition is used that has a self-etching function of concurrently executing the acid treatment and the primer treatment.

When the dental adhesive composition having the self-etching function is used, no problem arises such as any excessive demineralization of the enamel and denaturing of the collagen of the dentine, and the operation of the dental adhesive composition is simple. Therefore, many product lines thereof are put in the market.

Recently, fluorine tends to be applied to tooth surfaces in dental clinics and toothpaste with fluoride tends to be used in brushing teeth in the home due to the improvement of the preventive attention by patients and dentists. Thus, a tendency is recognized to improve the acid resistivity of the tooth surface. In the case where the acid resistivity of the tooth surface is improved as above, it is worried that the adhesive strength is degraded when only the dental adhesive composition having the self-etching function is applied. Especially, for a pit and fissure plugging material or an orthotic material to be adhered to unground enamel, the application of only the dental adhesive composition having the self-etching function results in an insufficient demineralization action, and a serious problem of degradation of the adhesiveness arises.

With the above in the background, acid etching materials have been proposed as follows whose damage to the tooth surface due to the demineralization is reduced by reducing the acidity thereof.

For example, Japanese Patent Publication No. 5-163111 proposes a technique according to which stimulation to the tooth pulp is reduced by retaining partially a dentinal plug that is present on the dentine surface after formation of a cavity by using a dental pre-treatment agent including a water solution of organic carboxylic acid and iron phosphate. Japanese Patent Publication No. 5-246817 proposes a technique according to which any excessive demineralization of the dentine after formation of a cavity and the tooth pulp damaging property is weakened by using a dental acid treatment agent formed by solving a polymeric compound that has a carboxyl group in its molecule and whose molecular weight is 1,000 to 500,000 into water, alcohol, or a solvent mainly including a mixture of these. With these techniques, however, the damage to the dentine is reduced weakening the acidity while a problem rises that the adhesiveness is insufficient for the unground enamel or the enamel after the formation of the cavity.

Japanese Patent Publication No. 10-81611 proposes a technique according to which the denaturing of the collagen in the surface layer of the dentine after the demineralization is suppressed and adhesion inhibition due to shrinkage of the collagen is prevented by using a dental pre-treatment agent including an acidic water solution that has a phosphate solved therein and whose pH is equal to or lower than three. With this technique, however, the acidic water solution is used whose viscosity is low and whose permeability into the dentine is high, and the demineralized portion therefore is not limited to the inside of the surface layer of the dentine and reaches a deep portion thereof. As a result, a problem arise that a damaging action for the tooth pulp, etc., tends to be generated.

On the other hand, Japanese Patent No. 3505182 discloses a technique that high adhesive strength for enamel and dentine is obtained simultaneously with facilitating a polymerization reaction of a dental adhesive composition used after acid treatment, by adding a polymerization catalyst to an acid etching material. Similarly to the invention of the above '611 publication, the invention of the above '182 publication provides a treatment agent whose viscosity is low and whose permeability into the dentine is high, and the demineralized portion therefore is not limited to the inside of the surface layer of the dentine and reaches a deep portion thereof. As a result, a problem arises that a damaging action for the tooth pulp, etc., tends to be generated. Similarly, when this treatment agent is used for the enamel, a problem is recognized that this treatment agent tends to excessively demineralize. With the invention of the above '182 publication, a problem arises that the adhesiveness is significantly degraded for either the dentine or the enamel depending on the type of used polymerization catalyst.

SUMMARY OF THE INVENTION

Problems to be Solved by the Invention

An object of the present invention is to solve the above problems involved in the related art. In addition, an object of the present invention is to provide a dental conditioning composition that enhances the adhesiveness of any dental material for a tooth surface by suppressing any excessive demineralization for the tooth surface and improving the polymerization activity of a dental adhesive composition by retaining a polymerization catalyst which is included in the dental conditioning composition of the present invention on the tooth surface.

Means for Solving Problems

The inventors actively studied to solve the problems, as a result, found that the problems were able to be solved and any excessive demineralization of the tooth surface was able to be suppressed and completed the present invention. In more detail, the problems were solved by using a dental conditioning composition that includes a polymerization catalyst, an acidic compound, water, and a thickening material, wherein the dental conditioning composition has a gel character, and has pH (the hydrogen-ion exponent) that is in a range from 0.1 to 0.9.

Even when pH is low and the acidity is high like those of the dental conditioning composition of the present invention, the composition has the gel character and the composition can therefore be held on the surface layer of the target portion and the permeation of the dental conditioning composition into the tooth surface can be limited to the inside of the surface layer thereof. Any damaging action for the tooth pulp can therefore be prevented. For example, the dental conditioning composition according to the present invention can be held even on the tooth surface inside a cavity having a complicated figure, and the target portion therefore can sufficiently be demineralized without generating any secondary dental caries due to flowing and permeation of the acidic composition to/in the outside of the target portion.

In addition, the dental conditioning composition of the present invention shows a gel character and, thereby, the dental conditioning composition can be applied to unground enamel, etc., using a dental syringe and is therefore excellent in the operability.

The inventors found that, due to the addition of the polymerization catalyst to the dental conditioning composition of the present invention, even after washing of the dental conditioning composition with water and removal thereof, the polymerization catalyst was caused to remain on the tooth surface or the cavity surface by a mutual action of hydroxyapatite and collagen on the tooth surface or the cavity surface, and the polymerization activity of the dental adhesive composition was improved by the remaining polymerization catalyst.

The inventors also found that, in a preferred embodiment, more excellent adhesiveness is achieved for both of dentine and enamel by using barbituric acid as the polymerization catalyst.

The present invention therefore can suppress any flowing of the composition to the outside of the target portion, can suppress any excessive demineralization for the tooth surface, and can achieve a sufficient demineralization action. The dental conditioning composition can be acquired that improves the adhesiveness of any dental material for the tooth surface by improving the polymerization activity of the dental adhesive composition by causing the polymerization catalyst included in the dental conditioning composition of the present invention to remain on the tooth surface.

Effect of the Invention

The inventors can provide the dental conditioning composition that enhances the adhesiveness of any dental material for the tooth surface by suppressing any excessive demineralization for the tooth surface and improving the polymerization activity of the dental adhesive composition by causing a polymerization catalyst included in the dental conditioning composition of the present invention to remain on the tooth surface.

The dental conditioning composition of the present invention can improve the adhesive strength for the fluorinated enamel whose acid resistivity is improved and, for the dentine, can prevent the denaturing of the organic component (collagen) in the dentine, and can prevent induction of degradation of the adhesive strength due to the shrinkage of the collagen during the air-drying.

The present invention provides a dental conditioning composition that presents excellent adhesive strength for both of the dentine and the enamel, and the present invention is proper as a tooth surface treatment agent that concurrently treats the enamel and the dentine.

MODES FOR CARRYING OUT THE INVENTION

Figure 1:
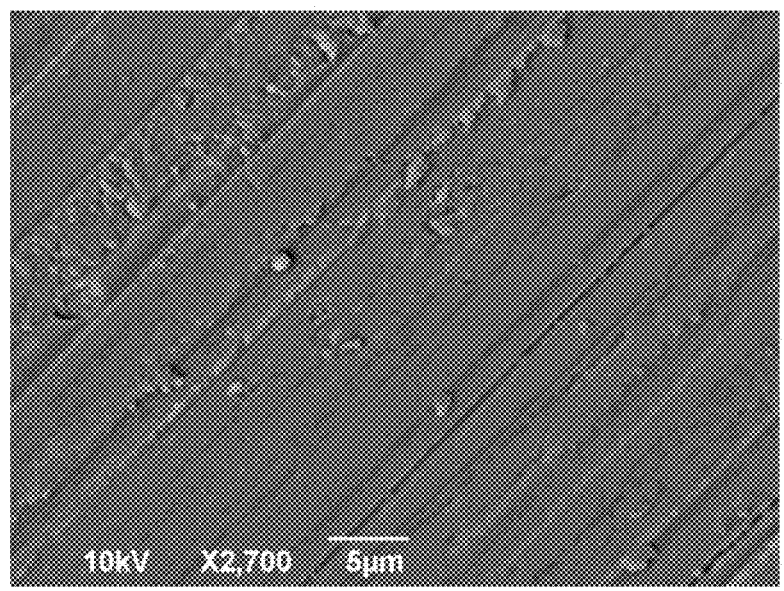
FIG. 1 is a diagram of a surface of enamel polished with #1200.

Components of the dental conditioning composition of the present invention are described in detail below.

Any acidic compound is usable without any limitation as an acidic compound usable in the dental conditioning composition of the present invention only in the case where the acidic compound is not a polymerizable monomer including an acidic group and presents acidity when the acidic compound is solved in water. When the acidic compound is the polymerizable monomer including an acidic group, the polymerizable monomer causes a certain reaction to take place with a co-existing polymerization catalyst to cause various problems such as, for example, a polymerization reaction of the polymerizable monomer including an acidic group, suppression of the activity of the polymerization catalyst, and degradation of the preservation stability due to change of the character of the composition. Examples of the acidic compound usable in the dental conditioning composition can be phosphoric acid, hydrochloric acid, citric acid, acetic acid, propionic acid, butyric acid, pentanoic acid, hexanoic acid, heptanoic acid, octanoic acid, tartaric acid, lactic acid, hydroxybenzoic acid, trihydroxybenzoic acid, benzenecarboxylic acid, phthalic acid, polyacrylic acid, polyitaconic acid, polymaleic acid, and any copolymer of these. Each of these acidic compounds alone or some thereof in combination may be blended.

The acidity of the acidic compound differs corresponding to the used compound and the amount of blended compound therefore is not especially limited. It is however necessary to blend the acidic compound such that pH of the dental conditioning composition is in a range from 0.1 to 0.9. Preferably, pH of the dental conditioning composition is 0.1 to 0.5.

Setting the pH value in these ranges enables sufficient adhesiveness to be acquired for unground enamel whose acid resistivity is improved by the application of fluorine, etc., and also enables prevention of any excessive demineralization of the unground enamel and any denaturing of collagen. As a result, sufficient adhesiveness is presented for dentine and any damaging action for the tooth pulp can be prevented.

Any known method in the technical field can be employed as the measurement method of pH. For example, the dental conditioning composition is diluted tenfold with ion-exchanged water, pH of this diluted solution is measured using a glass electrode hydrogen ion concentration meter, and a value obtained by subtracting 1.0 from the measured pH value can be taken as the pH value of the dental conditioning composition of the present invention.

It is important to add a gel character to the dental conditioning composition of the present invention by blending therein a thickening material such as colloidal silica, glycerin, or polyethyleneglycol. The compounding amount of thickening material is in a range from 2-20% by weight to 100% by weight of the dental conditioning composition, preferably, is in a range from 3-15% by weight, and, more preferably, is in a range from 4-10% by weight. Blending the thickening material in these ranges enables the permeability of the dental conditioning composition to properly be maintained for the tooth surface without degrading the viscosity of the dental conditioning composition, and enables prevention of any excessive demineralization. Any degradation of the adhesiveness for the dentine and any damaging action for the tooth pulp can therefore be prevented that are caused by the excessive demineralization of the enamel and the denaturing of the collagen. Viscosity of the dental conditioning composition can further be acquired with which the dental conditioning composition can be applied directly from a container such as a bottle or a syringe. Even during washing with water, the dental conditioning composition presents the viscosity with which the dental conditioning composition can be removed from the tooth surface, and the dental conditioning composition therefore presents excellent operability. The permeation of the dental conditioning composition sufficiently advances for the tooth surface and a demineralization action can effectively be produced.

The viscosity of the dental conditioning composition can be evaluated based on its flowing distance. The flowing distance and the viscosity are in the relation that the flowing distance is decreased when the viscosity is increased, and the flowing distance is increased when the viscosity is decreased. The flowing distance of the dental conditioning composition can be acquired by using a method described in Examples and, when the flowing distance is in a range from 0 to 5 mm, the dental conditioning composition is usable without any problem. Preferably, the flowing distance is in a range from 0 to 3 mm and, more preferably, is in a range from 0 to 2 mm. For example, the flowing distance may be in a range from 0.1 to 3 mm.

When a flowing distance in the above ranges is presented, the dental conditioning composition has sufficient viscosity and has the gel character defined in the present invention. Having the gel character enables the composition to be held on the surface layer of the target portion and also enables the permeation of the dental conditioning composition into the tooth surface to be limited to the inside of the surface layer. Any excessive demineralization of the enamel can therefore be prevented and the adhesive strength for the enamel can be improved. For the dentine, the denaturing of the organic component (collagen) in the dentine and induction of degradation of the adhesive strength due to the shrinkage of the collagen during the air-drying can be prevented, and the adhesive strength for the dentine can be improved. Any damaging action for the tooth pulp, etc., can further be prevented.

The dental conditioning composition according to the present invention can be held even on the tooth surface inside a cavity having a complicated structure, and any induction of any secondary dental caries, etc., due to flowing and permeation of the acidic composition to/in the outside of the target portion can therefore be prevented.

In addition, the dental conditioning composition of the present invention has the gel character while the dental conditioning composition has the viscosity with which, for example, the dental conditioning composition can be applied using a syringe, and also has the viscosity with which the dental conditioning composition can be statically left on the surface of a tooth after its application. More advantageously, the dental conditioning composition of the present invention has thixotropy.

The polymerization catalyst usable in the dental conditioning composition of the present invention is not especially limited, and any known radical generating agent is used without any limitation. The types of the polymerization catalyst are roughly classified into chemical polymerization catalysts and photo polymerization catalysts while each of these alone or some thereof in combination is/are usable regardless of the polymerization type.

The chemical polymerization catalyst can be the series of redox-type polymerization catalysts each including an organic peroxide/an amine compound, an organic peroxide/ an amine compound/a sulfinate, an organic peroxide/an amine compound/barbituric acid, or an organic peroxide/an amine compound/a borate compound, and the series of polymerization catalysts that each cause polymerization to start by reacting with oxygen or water such as organic boron compounds, perborate salts, permanganate salts, and persulfate salts.

Specific examples of the organic peroxide can be benzoyl peroxide, parachlorobenzoyl peroxide, 2,4-dichlorobenzoyl peroxide, acetyl peroxide, lauroyl peroxide, tertiary-butyl peroxide, cumenehydro peroxide, 2,5-dimethylhexane-2,5-dihydro peroxide, methylethylketone peroxide, and tertiary-butyl-peroxybenzoate.

Preferably, secondary or tertiary amine formed by an amino group bonded to an aryl group is used as the amine compound, and specific examples thereof can be N,N-dimethyl-p-toluidine, N,N-dimethylaniline, N-β-hydroxyethyl-aniline, N,N-di(β-hydroxyethyl)-aniline, N,N-di(β-hydroxyethyl)-p-toluidine, N-methyl-aniline, and N-methyl-p-toluidine.

Specific examples of sulfinate salt can be sodium benzenesulfinate, lithium benzenesulfinate, and sodium p-toluenesulfinate.

Specific examples of the borate compound can be sodium salts, lithium salts, potassium salts, magnesium salts, tetrabutylammonium salts, and tetramethylammonium salts of trialkylphenylboronate and trialkyl(p-phlorophenyl)borate (alkyl groups are an n-butyl group, an n-octyl group, an n-dodecyl group, etc.).

Specific examples of the organic boron compound can be triphenylborane, tributylborane, and a partially oxidized tributylborane. Specific example of perborate salt can be sodium-perborate. Specific examples of permanganate salt can be ammonium permanganate, potassium permanganate, and sodium permanganate. Specific examples of persulfate salt can be ammonium persulfate, potassium persulfate, and sodium persulfate.

Specific examples of barbituric acid can be barbituric acid, 1,3-dimethyl-barbituric acid, 1,3-diphenyl-barbituric acid, 1,5-dimethyl-barbituric acid, 5-butyl-barbituric acid, 5-ethyl-barbituric acid, 5-isopropyl-barbituric acid, 5-cyclohexyl-barbituric acid, 1,3,5-trimethyl-barbituric acid, 1,3-dimethyl-5-ethyl-barbituric acid, 1,3-dimethyl-n-butyl-barbituric acid, 1,3-dimethyl-5-isobutyl-barbituric acid, 1,3-dimethyl-5-tert-butyl-barbituric acid, 1,3-dimethyl-5-cyclopentyl-barbituric acid, 1,3-dimethyl-5-cyclohexyl-barbituric acid, 1,3-dimethyl-5-phenyl-barbituric acid, 1-cyclohexyl-5-ethyl-barbituric acid, 1-benzyl-5-phenyl-barbituric acid, thio-barbituric acids, N-cyclohexyl-5-propyl-barbituric acid, and salts of these (preferably, especially, those each with an alkali metal or an alkali earth metal are usable) such as, for example, sodium 5-butyl-barbituric acid, sodium 1,3,5-trimethyl-barbituric acid, calcium 1,3,5-trimethyl-barbituric acid, and sodium 1-cyclohexyl-5-ethyl-barbituric acid.

The photo polymerization catalyst can be those each including a system of only a photo sensitization agent, or those each including a combination of a photo sensitization agent and a photo polymerization accelerator.

Specific examples of the photo sensitization agent usable as the photo polymerization catalyst can be α-diketones such as benzil, camphorquinone, α-naphthyl, acetonaphthene, p,p'-dimethoxybenzil, p,p'-dichlorobenzilacetyl, petanedione, 1,2-phenanthrenequinone, 1,4-phenanthrenequinone, 3,4-phenanthrenequinone, 9,10-phenanthrenequinone, and naphthoquinone, benzoinalkylethers such as benzoin, benzoinmethylether, and benzoinethylether, thioxanthones such as thioxanthone, 2-chlorothioxanthone, 2-methylthioxanthone, 2-isopropylthioxanthone, 2-methoxythioxanthone, 2-hydroxythioxanthone, 2,4-diethylthioxanthone, and 2,4-diisopropylthioxanthone, benzophenones such as benzophenone, acetoinbenzophenone, p-chlorobenzophenone, and p-methoxybenzophenone, acylphosphine oxides such as 2,4,6-trimethylbenzoyldiphenylphosphine oxide and bis(2,6-dimethoxybenzoyl)-2,4,4-trimethylpentylphosphine oxide, α-aminoacetophenones such as 2-benzyl-dimethylamino-1-(4-morpholinophenyl)-butanone-1, and 2-benzyl-diethyl-amino-1-(4-morpholinophenyl)-propanone-1, ketals such as benzyldimethylketal, benzyldiethylketal, and benzyl(2-methoxyethylketal), and titanocenes such as bis(cyclopentadienyl)-bis[2,6-difluoro-3-(1-pyrrolyl)phenyl]-titanium, bis(cyclopentadienyl)-bis(pentanefluorophenyl)-titanium, and bis(cyclopentadienyl)-bis(2,3,5,6-tetrafluoro-4-disiloxyphenyl)-titanium.

Specific examples of the photo polymerization accelerator usable as the photo polymerization catalyst can be tertiary amines such as N,N-dimethylaniline, N,N-diethylaniline, N,N-di-n-butylaniline, N,N-dibenzylaniline, N,N-dimethyl-p-toluidine, N,N-dimethyl-m-toluidine, N,N-diethyl-p-toluidine, p-bromo-N,N-dimethylaniline, m-chloro-N,N-dimethylaniline, p-dimethylaminobenzaldehyde, p-dimethylaminoacetophenone, p-dimethylamino-benzoic acid, p-dimethylamino-benzoic acid-ethylester, p-dimethylamino-benzoic acid-aminoester, N,N-dimethyl-anthranilic acid-methylester, N,N-dihydroxyethylaniline, N,N-dihydroxyethyl-p-toluidine, p-dimethylaminophenylalcohol, p-dimethylaminostyrene, N,N-dimethyl-3,5-xylidine, 4-dimethylaminopyridine, N,N-dimethyl-α-naphthylamine, N,N-dimethyl-β-naphthylamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, N,N-dimethylaminoethylmethacrylate, N,N-diethylaminoethylmethacrylate, and 2,2'-(n-butylimino) diethanol, secondary amines such as N-phenylglycine, barbituric acids such as 5-butyl-barbituric acid, 1-benzil-5-phenyl-barbituric acid, 1,3,5-trimethyl-barbituric acid, sodium 1,3,5-trimethyl-barbiturate, and calcium acid 1,3,5-trimethyl-barbiturate, tin compounds such as dibutyltin-diacetate, dibutyltin-dilaurate, dioctyltin-dilaurate, dioctyltin-didecanoate, dioctyltin-bis(mercaptoacetic acid-isooctylester) salt, and tetramethyl-1,3-diacetoxydistanoxan, aldehyde compounds such as laurylaldehyde and terephthalaldehyde, and sulfur-including compounds such as dodecylmercaptan, 2-mercaptobenzoxazole, 1-decanethiol, and thiosalicylic acid.

Of these polymerization catalysts, from the view points of the tendency of the dental conditioning composition to remain on the surfaces of a tooth and a cavity due to the mutual action of hydroxyapatite and collagen on these surfaces even after the dental conditioning composition is washed with water and is removed, and contribution to the polymerization reaction with a dental adhesive composition, preferably, the barbituric acid capable of being expressed in a general formula [1] below or its derivative and, more preferably, 5-bytyl-barbituric acid, 1,3,5-trimethyl-barbituric acid, 1-cyclohexyl-5-ethyl-barbituric acid, and 1-benzyl-5-phenyl-barbituric acid are used.

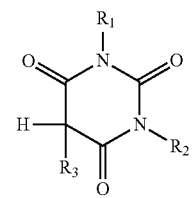

[1]

wherein, R1, R2, and R3 may be same as each other or may differ from each other, and each denote an aliphatic, an aromatic, an alicyclic or a heterocyclic residue that may include a substituent group such as a halogen atom, an alkyl group, an alkoxy group, an aryl group, or a cyclohexyl group, or a hydrogen atom.

The compounding amount of polymerization catalyst used in the dental conditioning composition of the present invention is in a range from 0.1 to 25% by weight to 100% by weight of the dental conditioning composition, preferably, is in a range from 0.2 to 10% by weight, and, more preferably, is in a range from 0.5 to 2.0% by weight. Setting the amount of the blended polymerization catalyst to be in these ranges provides excellent adhesiveness.

Any water is usable as the water usable in the dental conditioning composition of the present invention only when the water is clinically accepted as a medical component and does not essentially include any impurity that is harmful to the components and the adhesive effect of the dental conditioning composition of the present invention. Preferably, for example, distilled water (or purified water) or ion-exchanged water (or deionized water) is used. The compounding amount of water is an amount acquired by subtracting the total amount of the blended polymerization catalyst and the blended acidic compound from 100% by weight, and the amount thereof is in a range from 10 to 98% by weight. Preferably, this amount is in a range from 20 to 70% by weight and, more preferably, is in a range from 30 to 60% by weight. Because the compounding amount of water is in these ranges, the permeability of the dental conditioning composition for the tooth surface can properly be maintained without degrading the viscosity of the dental conditioning composition and any excessive advancement of the demineralization can be prevented. Any degradation of the adhesiveness for the dentine and any damaging action for the tooth pulp due to excessive demineralization of the enamel and denaturing of collagen can therefore be prevented. Excellent adhesiveness can be maintained for unground enamel whose acid resistivity is improved by application of fluorine, etc.

A coloring material can also be blended in the dental conditioning composition of the present invention. The type and the concentration of the coloring material are not especially limited while, preferably, the presence of the dental conditioning composition can easily be distinguished by visual observation when the dental conditioning composition is applied to a tooth surface, and it can be checked that no dental conditioning composition remains on the tooth surface by visual observation when the dental conditioning composition is washed with water.

Specific examples of an inorganic coloring material usable in the dental conditioning composition of the present invention can be chromate salts such as chrome yellow, zinc yellow lead, and barium yellow, ferrocyanides such as ferric hexacyanoferrate, sulfides such as cinnabar mercury, cadmium yellow, zinc sulfide, antimony white, and cadmium red, hydrosulfates such as barium sulfate, zinc sulfate, and strontium sulfate, hydroxides such as zinc flower, titanium white, colcothar, iron black, and chrome oxide, hydroxides such as aluminum hydroxide, silicate salts such as calcium silicate and ultramarine blue, and carbon such as carbon black and graphite.

Specific examples of an organic coloring material usable in the dental conditioning composition of the present invention can be nitroso-based pigments such as naphthol green B and naphthol green Y, nitro-based pigments such as naphthol S, and lithol-fast yellow 2G, insoluble azo-based pigments such as permanent red 4R, brilliant fast scarlet, hansa yellow, and benzidine yellow, low-solubility azo-based pigments such as lysol red, lake red C, and lake red D, soluble azo-based pigments such as brilliant carmine 6B, permanent red FSR, pigment scarlet 3B, and Bordeaux 10B, phthalocyanine-based pigments such as phthalocyanine blue, phthalocyanine green, and sky blue, basic dye-based pigments such as rhodamine lake, malachite green lake, and methyl violet lake, and acidic dye-based pigments such as peacock blue lake, eosin lake, and quinoline yellow lake.

Such components can arbitrarily be added as necessary to the dental conditioning composition, as a fluorine sustained release material, a coloring prevention agent, an antibacterial material, and any other traditionally known additives. The packaging form of the dental conditioning composition of the present invention is not especially limited, and any one of a one-pack packaging form, a two-pack packaging form, and another form may be used. The packaging form can be selected corresponding to the use.

EXAMPLES

The present invention is described in more detail with reference to Examples and Comparative Examples while the present invention is not limited to these.

Testing methods are as follows to evaluate the performance of the dental conditioning compositions prepared in Examples and Comparative Examples.

(1) Production of Embedded Enamel (Enamel with Improved Acid Resistivity) for Adhesion Test A central incisor was removed that was a permanent tooth on the lower jaw of a cow after being slaughtered, and was frozen and stored within 24 hours after the removal thereof. After the tooth was thawed, the tooth root thereof was removed and the tooth crown was cut off to produce small slips of the cow tooth. The small slip of the cow tooth was embedded in an epoxy resin. Under pouring water, the enamel of the embedded cow tooth was exposed using a waterproof abrasive paper of #600. Thereafter, the small slip of the cow tooth with its enamel exposed was immersed in a water solution of sodium fluoride (fluorine concentration: 1,000 ppm) for one month to produce enamel with improved acid resistivity.

(2) Production of Embedded Dentine for Adhesion Test

Dentine of another tooth of the cow cut and embedded similarly to the enamel of the tooth of the cow was exposed under pouring water using a waterproof abrasive paper of #600.

(3) Adhesion Test

The enamel and the dentine both with the improved acid resistivity were dried. A strip of double-sided tape with a hole having a diameter of 4 mm is attached to the exposed enamel or dentine to define the surface for adhesion. The dental conditioning composition of each of Examples or Comparative Examples was applied to the defined surface for adhesion. After 30 sec, washing with water and drying were executed therefor. Thereafter, an adhesion process was executed therefor using "BeautiBond Multi" that was a dental adhesive composition having a self-etching function, according to the method instructed by the manufacturer thereof. Thereafter, a plastic mold (inner diameter: 4 mm, height: 2 mm) was fixed to the surface applied with the adhesion process, and the inside of the mold was filled with a photo polymerization composite resin (BeautiFill II, manufactured by Shofu Inc.). The photo polymerization composite resin was hardened by applying a light beam for 20 sec using a photo polymerization irradiator (Grip Light II, manufactured by Shofu Inc.). After the hardening, the mold was removed to acquire an adhesion test piece. The adhesion test piece was immersed in distilled water at 37° C. for 24 hours and, thereafter, a tooth substance adhesiveness test was conducted based on shear adhesive strength at a cross head speed of 1 ram/min using an Instron universal testing machine (Instron 5567, manufactured by Instron). The number of test pieces was set to be 6 and the average of the acquired values was taken as the value of the adhesive strength. No tooth surface conditioning process was executed for Comparative Example 1, and the adhesion operation using BeautiBond Multi and the filling operation using BeautiFill II were executed therefor.

(4) Fluidity Test 0.03 g of the dental conditioning composition was statically put on a glass plate and, thereafter, the glass plate was vertically held for 30 sec. After 30 sec, the flowing distance was measured for which the dental conditioning composition had flowed.

(5) Observation of Treated Surface

A central incisor was removed that was a permanent tooth on the lower jaw of a cow after being slaughtered, and was frozen and stored within 24 hours after the removal thereof. After the tooth was thawed, the tooth root thereof was removed and the tooth crown was cut off to produce small slips of the cow tooth. The small slip of the cow tooth was embedded in an epoxy resin. Under pouring water, the enamel of the embedded cow tooth was exposed using a waterproof abrasive paper of #600, and final polishing was executed therefor using a waterproof abrasive paper of #1200. The polished surface was treated with the dental conditioning composition for 30 sec, and washing with water and drying were executed for the treated surface.

Surface observation was executed for the treated surface using a scanning electron microscope (SEM).

(6) Measuring Method of pH of Dental Conditioning Composite

The dental conditioning composite was diluted tenfold with ion-exchanged water, pH of this diluted solution was measured using a glass electrode hydrogen ion concentration meter (pH METER F-22, manufactured by Horiba Ltd.), and a value acquired by subtracting 1.0 from the measured pH value was taken as the pH value of the dental conditioning composition.

The names of the components used in Examples and Comparative Examples of the present invention and their abbreviations are listed below.
PAA: Polyacrylic acid
TMBA: 1,3,5-trimethyl-barbituric acid
CPBA: N-cyclohexyl-5-propyl-barbituric acid
200: AEROSIL (a registered trademark) 200

Table 1 shows the composition of each of the dental conditioning compositions used in Examples and Comparative Examples.

TABLE 1

| | Dental conditioning composition | | | | | | | |
|---|---|---|---|---|---|---|---|---|
| | Component | | | | | | | |
| | Acidic Compound | | | | Polymerization Catalyst | | Thickening Material | Water Purified |
| | PAA | Tartaric Acid | Lactic Acid | Phosphoric Acid | TMBA | CPBA | #200 | Water |
| Composition 1 | 10.0 | 45.0 | — | — | 1.0 | — | 10.0 | 34.0 |
| Composition 2 | 5.0 | 22.5 | — | — | 1.0 | — | 10.0 | 61.5 |
| Composition 3 | — | — | 40.0 | — | 1.0 | — | 10.0 | 49.0 |
| Composition 4 | — | — | 70.0 | — | 1.0 | — | 10.0 | 19.0 |
| Composition 5 | | | 80.0 | | 1.0 | — | 5.0 | 14.0 |
| Composition 6 | 10.0 | 45.0 | — | — | 1.0 | — | 5.0 | 39.0 |
| Composition 7 | 10.0 | 45.0 | — | — | 1.0 | — | 15.0 | 29.0 |
| Composition 8 | 10.0 | 45.0 | — | — | 5.0 | — | 10.0 | 30.0 |
| Composition 9 | 10.0 | 45.0 | — | — | 0.2 | — | 10.0 | 34.8 |
| Composition 10 | 10.0 | 45.0 | — | — | — | 1.0 | 10.0 | 34.0 |
| Composition C2 | 2.5 | 11.0 | — | — | 1.0 | — | 10.0 | 75.5 |
| Composition C3 | — | — | 30.0 | — | 1.0 | — | 10.0 | 59.0 |
| Composition C4 | — | — | 90.0 | — | 1.0 | — | — | 9.0 |
| Composition C5 | — | — | — | 30.0 | 1.0 | — | — | 69.0 |
| Composition C6 | 10.0 | 45.0 | — | — | 1.0 | — | 21.0 | 23.0 |
| Composition C7 | 10.0 | 45.0 | — | — | — | — | 10.0 | 35.0 |
| Composition C8 | 12.0 | 45.0 | — | — | 1.0 | — | 20.0 | 22.0 |
| Composition C9 | 10.0 | 45.0 | — | — | 1.0 | — | — | 44.0 |
| Composition C10 | — | — | 85.0 | — | 1.0 | — | 10.0 | 4.0 |
| Composition C11 | 1.0 | — | — | — | 1.0 | — | 13.0 | 85.0 |

Table 2 shows the test results concerning the dental conditioning compositions of Examples and Comparative Examples.

TABLE 2

| | | | Flowing Distance | | Adhesive Strength [MPa] | |
|---|---|---|---|---|---|---|
| | Composition | pH | [mm] | Character | Enamel*[1] | Dentine |
| Example 1 | Composition 1 | 0.5 | 0.8 | gel | 16.3 | 14.3 |
| Example 2 | Composition 2 | 0.9 | 0.9 | gel | 13.8 | 14.2 |
| Example 3 | Composition 3 | 0.8 | 1.0 | gel | 13.5 | 15.5 |
| Example 4 | Composition 4 | 0.5 | 1.1 | gel | 16.2 | 15.5 |
| Example 5 | Composition 5 | 0.1 | 1.7 | gel | 17.3 | 13.1 |
| Example 6 | Composition 6 | 0.5 | 1.8 | gel | 14.8 | 15.2 |
| Example 7 | Composition 7 | 0.5 | 1.1 | gel | 15.6 | 12.8 |
| Example 8 | Composition 8 | 0.5 | 1.0 | gel | 16.2 | 13.8 |
| Example 9 | Composition 9 | 0.5 | 1.0 | gel | 14.3 | 15.2 |
| Example 10 | Composition 10 | 0.5 | 0.9 | gel | 17.2 | 15.3 |
| Comp. Exam. 1 | — | — | — | — | 5.0 | 12.1 |
| Comp. Exam. 2 | Composition C2 | 1.3 | 1.0 | gel | 7.2 | 14.8 |
| Comp. Exam. 3 | Composition C3 | 1.1 | 0.7 | gel | 8.5 | 15.2 |
| Comp. Exam. 4 | Composition C4 | 0.05 | 5.2 | liquid | 19.5 | 7.5 |
| Comp. Exam. 5 | Composition C5 | 0.1 | 9.5 | liquid | 16.2 | 6.7 |
| Comp. Exam. 6 | Composition C6 | 0.6 | 0 | solid | 11.7 | 14.3 |
| Comp. Exam. 7 | Composition C7 | 0.5 | 0.8 | gel | 14.6 | 9.0 |
| Comp. Exam. 8 | Composition C8 | 0.5 | 0 | solid | 6.0 | 14.1 |
| Comp. Exam. 9 | Composition C9 | 0.5 | 9.7 | liquid | 18.1 | 8.2 |
| Comp. Exam. 10 | Composition C10 | 0.05 | 1.2 | gel | 17.4 | 6.8 |
| Comp. Exam. 11 | Composition C11 | 2.7 | 1.4 | gel | 5.6 | 12.9 |

*Enamel immersed in a sodium fluoride water solution (fluorine concentration: 1,000 ppm) for one month.

As shown in Table 2, the dental conditioning compositions of Examples 1 to 10 each presented pH in a range from 0.1 to 0.9, each achieved an excellent demineralization action even for the enamel with the improved acid resistivity, and each had improved adhesive strength for the enamel. The flowing distances of the dental conditioning composites were in a range from zero to 1.8 mm, and the dental conditioning compositions did not therefore permeate into the deep portion of the dentine and did not denature the collagen fibers, and the collagen did not shrink during air-drying. Excellent adhesive strength for the dentine was recognized. Due to the effect of the polymerization catalyst added to the dental conditioning compositions of Examples 1 to 10, the polymerization activity of BeautiBond Multi used after the acid treatment by the dental conditioning composition was improved and the adhesive strength was improved especially for the dentine.

On the other hand, Comparative Example 1 in Table 2 presented a result acquired by conducting the adhesion test without using the dental conditioning composition and using only BeautiBond Multi. The adhesive strength thereof was poor for the enamel whose acid resistivity was improved by the fluorination process and it was revealed that, when only BeautiBond Multi was applied without using the dental conditioning composition of the present invention, no sufficient demineralization action was acquired for the enamel with the improved acid resistivity.

For Comparative Examples 2 and 3, the amount of acidic compound blended in the dental conditioning composition was small and pH thereof was equal to or higher than 1.0. Due to this influence, the demineralization action was insufficient and the adhesive strength for the enamel with the improved acid resistivity was degraded. On the contrary, Comparative Example 4 had a large amount of acidic compound blended therein and pH thereof was lower than 0.1. As a result, the adhesive strength for the enamel with the improved acid resistivity was high while excessive demineralization was achieved for the dentine and the adhesive strength for the dentine was degraded.

Comparative Example 5 had no thickening material blended therein and the viscosity thereof was therefore degraded and the flowing distance thereof was 9.5 mm. Based on this, it is considered that the permeation of the dental conditioning composition may be facilitated for the dentine and the demineralization may be achieved up to the deep portion, resulting in the degradation of the adhesive strength for the dentine.

Comparative Example 6 had the thickening material excessively blended therein and the viscosity of the dental conditioning composition was therefore increased, and the character thereof was that of a solid. The ejection property of the dental conditioning composition from a syringe or a bottle was therefore significantly degraded. The permeation of the dental conditioning composition into the tooth surface was degraded and the adhesive strength for the enamel was therefore degraded.

Comparative Example 7 had no polymerization catalyst blended in the dental conditioning composition, and the polymerization activity of BeautiBond Multi used after the acid treatment using the dental conditioning composition was not improved. The adhesive strength for the dentine was degraded.

The composition of Comparative Example 8 was a solid and, similarly to Comparative Example 6, the ejection property of the dental conditioning composition from a syringe or a bottle was significantly degraded. The permeation of the dental conditioning composition into the tooth surface was degraded and the adhesive strength for the enamel was thereby significantly degraded.

Comparative Example 9 had no thickening material blended therein. The viscosity thereof was therefore reduced and the operability thereof was poor for treating a target portion. Similarly to Comparative Example 5, the deep portion of the dentine was demineralized and the adhesive strength therefor was degraded.

Though the composition of Comparative Example 10 was a gel, pH thereof was 0.05. According to the result of the adhesion test, the demineralization of the dentine was advanced and the adhesive strength for the dentine was degraded.

Though the composition of Comparative Example 11 was a gel, pH thereof was 2.7. According to the result of the adhesion test, the capacity for demineralization for the fluorinated enamel was insufficient and the adhesive strength was degraded.

(SEM Observation)

Figure 2:
FIG. 2 is a diagram of a surface of enamel treated by a dental conditioning composition of Example 1.

FIG. 1 shows the surface of #1200-polished enamel. FIG. 2 shows the surface of enamel treated by the dental conditioning composition described in Example 1. As is clear from FIG. 2, the surface of the enamel treated by the dental conditioning composition of the present invention removes the smear layer that is the cause of adhesion failure, and the demineralization is limited to the inside of the surface layer of the tooth substance.

INDUSTRIAL APPLICABILITY

The present invention provides the dental conditioning composition used in a tooth surface treatment executed before application of a dental adhesive composition when such a dental material is caused to adhere to the tooth surface using the dental adhesive composition, as an orthotic material, a pit and fissure plugging material, a restoration material, a dental crown material, a prosthetic material, a dental abutment construction material, or a root canal material.

The invention claimed is:

1. A dental conditioning composition having a gel character, comprising:
   a polymerization catalyst;
   an acidic compound;
   water; and
   a thickening material, wherein
   pH of the dental conditioning composition is in a range from 0.1 to 0.9,
   an amount of the thickening material is in a range from 5 to 15% by weight relative to 100% by weight of the dental conditioning composition, and
   a flowing distance of the dental conditioning composition is 0.1 to 3 mm.

2. The dental conditioning composition of claim 1, wherein
   the acidic compound is selected from a group including phosphoric acid, hydrochloric acid, citric acid, acetic acid, propionic acid, butyric acid, pentanoic acid, hexanoic acid, heptanoic acid, octanoic acid, tartaric acid, lactic acid, hydroxybenzoic acid, trihydroxybenzoic acid, benzenecarboxylic acid, phthalic acid, polyacrylic acid, polyitaconic acid, polymaleic acid, and any combination of these.

3. The dental conditioning composition of claim 1, wherein
   the polymerization catalyst is at least one selected from group consisting of barbituric acid, 1,3-dimethyl-barbituric acid, 1,3-diphenyl-barbituric acid, 1,5-dimethyl-barbituric acid, 5-butyl-barbituric acid, 5-ethyl-barbituric acid, 5-isopropyl-barbituric acid, 5-cyclohexyl-barbituric acid, 1,3,5-trimethyl-barbituric acid, 1,3-dimethyl-5-ethyl-barbituric acid, 1,3-dimethyl-n-butyl-barbituric acid, 1,3-dimethyl-5-isobutyl-barbituric acid, 1,3-dimethyl-5-tert-butyl-barbituric acid, 1,3-dimethyl-5-cyclopentyl-barbituric acid, 1,3-dimethyl-5-cyclohexyl-barbituric acid, 1,3-dimethyl-5-phenyl-barbituric acid, 1-cyclohexyl-5-ethyl-barbituric acid, 1-benzyl-5-phenyl-barbituric acid, thio-barbituric acid, N-cyclohexyl-5-propyl-barbituric acid, sodium 5-butyl-barbituric acid, sodium 1,3,5-trimethyl-barbituric acid, calcium 1,3,5-trimethyl-barbituric acid, and sodium 1-cyclohexyl-5-ethyl-barbituric acid.

4. The dental conditioning composition of claim 1, further comprising a coloring material.

* * * * *